(12) United States Patent
Oftring et al.

(10) Patent No.: US 9,227,915 B2
(45) Date of Patent: Jan. 5, 2016

(54) PROCESS FOR THE PREPARATION OF A CRYSTALLINE L-MGDA TRIALKALI METAL SALT

(75) Inventors: Alfred Oftring, Bad Duerkheim (DE); Maxim Weber, Limburgerhof (DE); Gerold Braun, Ludwigshafen (DE); Arnulf Lauterbach, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 433 days.

(21) Appl. No.: 13/463,446

(22) Filed: May 3, 2012

(65) Prior Publication Data

US 2012/0283473 A1 Nov. 8, 2012

Related U.S. Application Data

(60) Provisional application No. 61/481,763, filed on May 3, 2011.

(51) Int. Cl.
*C07C 227/42* (2006.01)

(52) U.S. Cl.
CPC .................................. *C07C 227/42* (2013.01)

(58) Field of Classification Search
CPC .................................................... C07C 227/42
See application file for complete search history.

(56) References Cited

U.S. PATENT DOCUMENTS

| 5,786,313 A | 7/1998 | Schneider et al. |
| 5,849,950 A * | 12/1998 | Greindl et al. ................ 562/571 |
| 5,981,798 A | 11/1999 | Schönherr et al. |
| 8,628,684 B2 * | 1/2014 | Mrzena et al. ............. 252/182.3 |
| 2011/0257431 A1 | 10/2011 | Baumann et al. |

FOREIGN PATENT DOCUMENTS

| CA | 2771916 A1 * | 3/2011 |
| DE | WO 2010133618 | * 11/2010 |
| EP | 0 845 456 A2 | 6/1998 |
| WO | WO 94/29421 A1 | 12/1994 |
| WO | WO 2011/042836 A1 | 4/2011 |
| WO | WO 2011/113822 A1 | 9/2011 |
| WO | WO 2012/136474 A1 | 10/2012 |
| WO | WO 2012/139842 A1 | 10/2012 |

OTHER PUBLICATIONS

Rouhi, Chemical and Engineering News, The Right Stuff, 2003, 81(8), pp. 32-35.*
Kirk-Othmer, Encyclopedia of Chemical Technology, 5th edition, Crystallization, 2007, John Wiley & Sons, pp. 95-147.*
U.S. Appl. No. 13/498,825, filed Mar. 28, 2012, Judat, et al.
U.S. Appl. No. 13/431,381, filed Mar. 27, 2012, Oftring, et al.
U.S. Appl. No. 13/430,105, filed Mar. 26, 2012, Baumann, et al.

* cited by examiner

*Primary Examiner* — Paul A Zucker
(74) *Attorney, Agent, or Firm* — Oblon, McClelland, Maier & Neustadt, L.L.P.

(57) ABSTRACT

A process is proposed for the preparation of a crystalline L-MGDA trialkali metal salt by crystallization from an aqueous solution thereof which has been obtained by Strecker synthesis, starting from L-α-alanine, by reaction with formaldehyde and hydrocyanic acid to give L-α-alanine-N,N-diacetonitrile and subsequent alkaline saponification of the L-α-alanine-N,N-diacetonitrile to give the L-MGDA trialkali metal salt, wherein a temperature of 150° C. is not exceeded during the alkaline saponification.

18 Claims, 2 Drawing Sheets
(2 of 2 Drawing Sheet(s) Filed in Color)

PROCESS FOR THE PREPARATION OF A CRYSTALLINE L-MGDA TRIALKALI METAL SALT

CROSS-REFERENCE TO RELATED APPLICATIONS

This patent application claims the benefit of U.S. provisional patent application Ser. 61/481,763 filed May 3, 2011 incorporated in its entirety herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

REFERENCE TO A "SEQUENCE LISTING," A TABLE, OR A COMPUTER PROGRAM LISTING APPENDIX SUBMITTED ON A COMPACT DISC AND AN INCORPORATION-BY-REFERENCE OF THE MATERIAL ON THE COMPACT DISC

Not Applicable.

BACKGROUND OF THE INVENTION

Complexing agents for alkaline earth metal ions and heavy metal ions are used in wide sectors of the industry, for example in the detergents and cleaners industry or in the treatment of metal surfaces. Usually, they are synthesized in aqueous solution. For certain applications, they are required in solid form.

Customary processes for the preparation of solids from aqueous solutions are in particular crystallization and spray-drying processes. It is known that crystalline solid as is produced, for example, during evaporation crystallization or cooling crystallization can comprise water of crystallization and, under ambient conditions, is in most cases less hygroscopic or storage-stable than amorphous solid. As a result of spray-drying processes, e.g. in the spray tower or in the spray fluidized-bed, by contrast, the solid is obtained in amorphous form. In this form, the solid is often highly hygroscopic and, in the event of open storage loses, within a short time, the ability to be poured, which considerably hinders the further processability, e.g. in tabletting presses, etc.

Methylglycinediacetic acid, referred to hereinbelow in abbreviated form as MGDA, also known as α-alaninediacetic acid (α-ADA), is a strong, readily biodegradable complexing agent for various technical applications and is known, e.g. from WO-A 94/29421.

In the form of the racemic trisodium salt mixture, the crystallization is severely inhibited by the asymmetric molecular form, which leads to correspondingly lengthy and uneconomical mass crystallization processes (evaporation crystallization and cooling crystallization).

EP-A 0 845 456 describes a process for producing MGDA-Na3 powders with an increased degree of crystallinity, in which the starting materials are in particular starting masses with water fractions of 10-30%, and preferably crystallization seeds are added. This process leads to predominantly crystalline powders, but, on account of the viscous and pasty phases during production, requires the use of complex and expensive mixer-kneader apparatuses in order to ensure conversion to the crystalline modifications.

Accordingly, it was an object of the invention to provide a technically simple process for the preparation of crystalline MGDA trialkali metal salts.

The solution consists in a process for the preparation of a crystalline L-MGDA trialkali metal salt by crystallization from an aqueous solution thereof which has been obtained by Strecker synthesis, starting from L-α-alanine, by reaction with formaldehyde and hydrocyanic acid to give L-α-alanine-N,N-diacetonitrile and subsequent alkaline saponification of the L-α-alanine-N,N-diacetonitrile to give the L-MGDA trialkali metal salt, wherein a temperature of 150° C. is not exceeded during the alkaline saponification.

Surprisingly, it has been found that the crystallization of L-MGDA trialkali metal salts proceeds with considerable advantages compared to the corresponding racemate, with corresponding applications-related advantages of the crystallizate.

BRIEF SUMMARY OF THE INVENTION

According to the invention, the starting material used is the L-enantiomer of α-alanine, which is reacted by Strecker synthesis with formaldehyde and hydrocyanic acid to give L-α-alanine-N,N-diacetonitrile, referred to hereinbelow in abbreviated form as L-ADAN. The L-ADAN is then saponified with a base to give the L-MGDA trialkali metal salt.

The Strecker synthesis can be carried out in any known manner, for example in accordance with the process disclosed in WO-A 94/29421.

BRIEF DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee.

Figure 1:
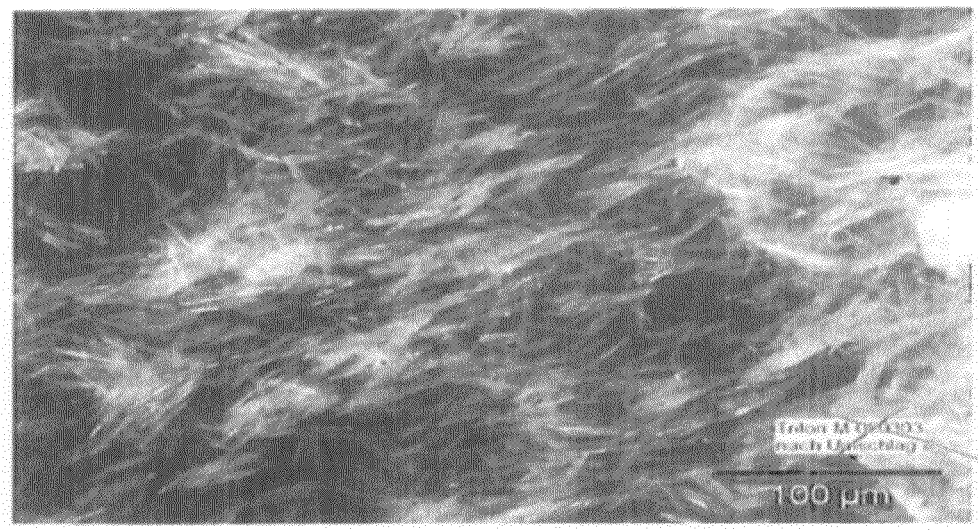
FIG. 1: a micrograph of the needles obtained according to the comparative example.

It can be seen in FIG. 1 that fine needles with a length below 100 μm were obtained.

Figure 2:
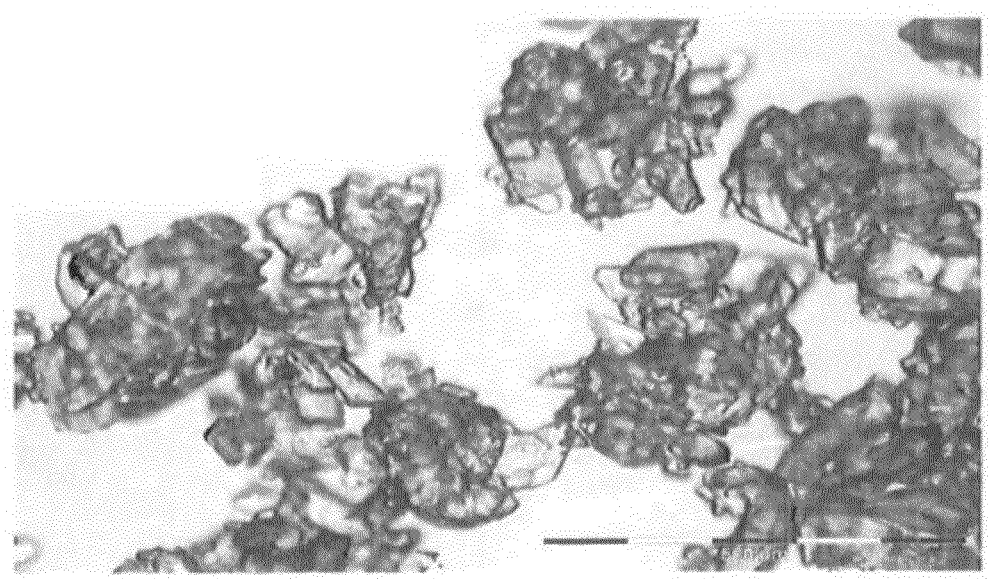
FIG. 2: a micrograph of the crystals obtained according to example 1
Figure 3:
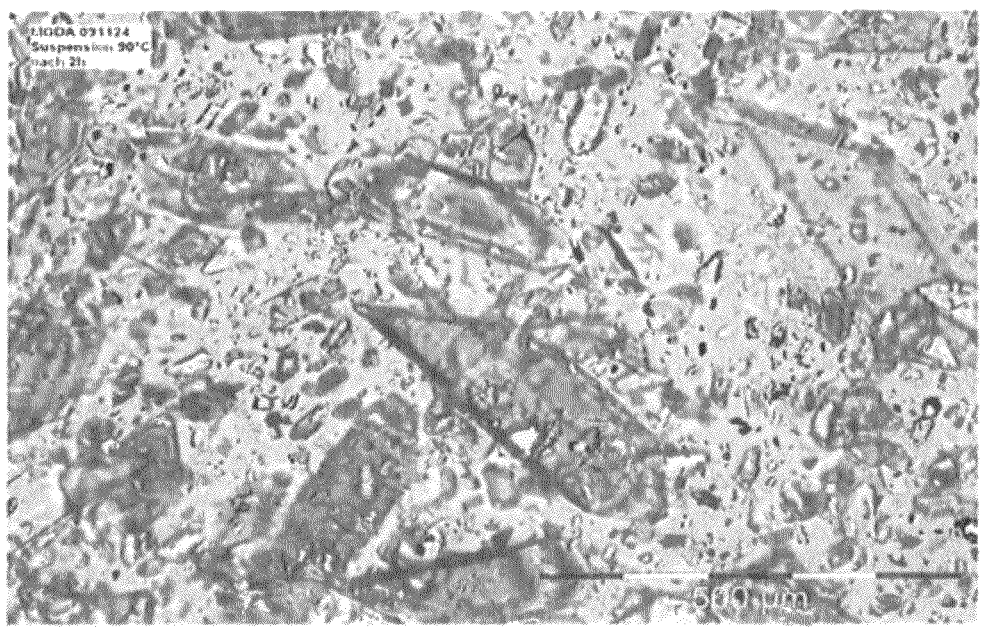
FIG. 3: a micrograph of the crystals obtained according to example 2.

By contrast, FIGS. 2 and 3 show distinct crystals.

DETAILED DESCRIPTION OF THE INVENTION

Irrespective of the specific Strecker synthesis procedure, it is essential for the present invention that the alkaline saponification of the L-ADAN always takes place under conditions which ensure that the L-MGDA trialkali metal salt obtained starting from L-α-alanine does not racemize. For this, it is sufficient to ensure that the temperature during the alkaline saponification does not exceed 150° C.

Advantageously, the temperature of the alkaline saponification should not exceed 130° C. It is particularly advantageous to carry out the alkaline saponification at a temperature which does not exceed 110° C.

The alkaline saponification of the L-ADAN can be carried out with sodium hydroxide solution. Accordingly, L-MGDA trisodium salts are obtained.

By the above process of the Strecker synthesis with subsequent alkaline hydrolysis, preferably L-MGDA trialkali metal salt solutions with a content of L-MGDA trialkali metal salt of at least 50% by weight, based on the total weight of the solution, or else of at least 40% by weight of MGDA trialkali metal salt, based on the total weight of the solution, are obtained. It has been found that the corresponding L-MGDA trialkali metal salt can be crystallized out of these solutions surprisingly easily.

For this purpose, an evaporation crystallization can advantageously be used.

The evaporation crystallization can advantageously be carried out continuously.

In another process variant, the evaporation crystallization can be carried out discontinuously.

Preferred process parameters both for the continuous and the discontinuous evaporation crystallization are temperatures in the range from 50 to 130° C., preferably in the range from 70 to 120° C., further preferably in the range from 80 to 100° C.

The continuous or discontinuous evaporation crystallization is advantageously carried out over a period from 1 to 24 hours, preferably from 5 to 24 hours, further preferably from 5 to 10 hours.

The evaporation rate, defined by the evaporation time and the crystal content at the end of the evaporation crystallization, is, for the continuous evaporation crystallization, in particular 1 to 50%, preferably 10 to 30% and further preferably 10 to 20%; for the discontinuous evaporation crystallization, in particular 1 to 60%, preferably 10 to 40%, further preferably 10 to 20%.

In another embodiment, the crystallization can be carried out by cooling crystallization.

The process is not limited with regard to the apparatuses in which the crystallization is carried out.

The invention also provides crystalline L-MGDA trialkali metal salts obtainable by the process described above.

Preference is given to the crystalline L-MGDA trialkali metal salt, a L-MGDA trisodium salt.

The crystallization according to the invention of the L-enantiomers of MGDA trialkali metal salts from their aqueous solutions has considerable advantages compared with crystallizations from the corresponding D,L-racemate: the crystals are formed gradually in the presence of seeds, which facilitates control of the crystallization. By contrast, the racemate crystallizes spontaneously in the event of high supersaturation, in which case inoculation brings about no significant improvement.

Compared with a crystallization from the solution of the racemate, in the case of the crystallization according to the invention from the solution of the L-enantiomer, better control of the solid content in the suspension is possible; as a result, the likelihood of faulty batches is lower, the crystallization apparatus does not become blocked.

Compared with a crystallization from a racemate solution, crystals with a considerably better morphology, and specifically three-dimensional particles, compared with needles, are obtained by the process according to the invention. This results in a considerably improved stirability of the suspensions and also substantially higher space-time yields. Thus, for example, a suspension with 12% by weight of D,L-MGDA trisodium salt needles is virtually solid, whereas one with 30% by weight of L-MGDA trisodium salt crystals is still readily stirable. Furthermore, the centrifugeability is better. On account of the smaller specific surface area, the purity is higher. Breakage in the case of three-dimensional particles is significantly lower than in the case of needles, and consequently also the fines fracture, and also the storage and transportation properties, are better. In particular, the crystals obtained in the process according to the invention are not hygroscopic, compared to a powder obtained for example by spray-drying.

The invention is illustrated in more detail below by reference to working examples and a drawing.

In each case, ca. 40% strength starting solutions of D,L-MGDA trisodium salt or L-MGDA trisodium salt, starting from D,L-α-alanine or L-α-alanine, respectively, were prepared as follows:

at ca. 40° C., 203 g of 30% strength formaldehyde (2.03 mol) were metered in, with cooling, to a solution of 178 g (2.0 mol) of α-alanine in 910 g of water (ca. 18% strength) over the course of ca. 60 minutes. Then, at ca. 40° C., 203 g of 30% strength formaldehyde (2.03 mol) and 109.6 g of hydrocyanic acid (4.06 mol) were metered into the resulting solution with cooling over the course of 60 minutes. The mixture was then left to after-react for 1 hour at 40° C. At ca. 30° C., this solution was then metered in to 496 g of 50% strength sodium hydroxide solution (6.20 mol) over the course of ca. 1 hour. Following after-stirring for two hours at 30° C., the temperature was increased to 95-102° C. and the conversion was completed over the course of ca. 4 hours, while simultaneously stripping off the ammonia formed and water. This gave 1330 g of a ca. 40% strength MGDA trisodium salt solution (MGDA-Na3). Yield: 98.2%; NTA-Na3 content: 0.06% (determination by means of HPLC)

COMPARATIVE EXAMPLE

Discontinuous Evaporation Crystallization of D,L-MGDA Trisodium Salt

In a 3 l crystallizer with agitator, 1200 g of a 40% strength D,L-MGDA trisodium salt solution were introduced as initial charge and, by means of evaporation, brought to saturation at 80° C. (46% for D,L-MGDA). The solution was then inoculated with ca. 0.5 g of the crystals from a previous experiment. Evaporation then followed at 80° C. with 50 g/h. No crystallization took place until, after the evaporation of 95 g, a massive seed shower resulted and the crystallizer was completely crystallized through. The suspension obtained in this way could no longer be stirred or filtered (theoretical solids fraction in the suspension at the end 9%). The crystals had the form of fine needles with a length below 100 μm.

EXAMPLE 1

Discontinuous Evaporation Crystallization of L-MGDA Sodium Salt

In a 3 l crystallizer with agitator, 2154 g of a 40% strength L-MGDA sodium salt solution were introduced as initial charge and evaporated to a concentration of 58%, which corresponds to a slight supersaturation at 80° C. the solution was then inoculated with 1% of the crystals, based on the solids content of the solution. The crystals were produced in a previous experiment. The evaporation then followed at 80° C. with 52 g/h. During the evaporation, well defined compact crystals were formed with a size of ca. 20-100 μm. The suspension could be readily stirred up to the end of the experiment (solids fraction in the suspension at the end 36%). The filter resistance ascertained during filtration was $2.25 \times 10^{13}$ mPas/m$^2$, i.e. the crystals can be separated off by filtration.

EXAMPLE 2

Continuous Evaporation Crystallization of L-MGDA Sodium Salt

At the start-up, 1280 g of the supersaturated 65% strength L-MGDA sodium salt solution were introduced as initial charge in a 1 l crystallizer with agitator. The solution was then inoculated in order to prepare a suspension. The continuous evaporation crystallization then followed at 90° C. with 454 g/h of feed and 204 g/h evaporation rate. This corresponds to a residence time of 5 h and a theoretical solids fraction in the suspension of 41%. During the evaporation, well defined compact crystals were formed with a size of ca. 10-500 μm. The suspension could be readily stirred to the end of the experiment. The filter resistance ascertained during the filtration was $12.7 \times 10^{13}$ mPas/m$^2$, i.e. the crystals can be separated off by filtration.

The invention claimed is:

1. A process for preparing a crystalline L-MGDA trialkali metal salt, the process comprising:
   (1) reacting enantiomerically enriched L-α-alanine with formaldehyde and hydrocyanic acid to give L-α-alanine-N,N-diacetonitrile; then
   (2) saponifying the L-α-alanine-N,N-diacetonitrile under alkaline conditions to give a L-MGDA trialkali metal salt; and
   (3) crystallizing the L-MGDA trialkyl metal salt from an aqueous solution,
   wherein
   a temperature of 150° C. is not exceeded during the saponifying (2) so that the L-MGDA trialkali metal salt does not racemize,
   and
   the L-MGDA trialkali metal salt is a L-MGDA trisodium salt or a L-MGDA tripotassium salt.

2. The process of claim 1, wherein a temperature of 130° C. is not exceeded during the saponifying (2).

3. The process of claim 1, wherein a temperature of 110° C. is not exceeded during the saponifying (2).

4. The process of claim 1, wherein the crystallizing (3) comprises an evaporation crystallization.

5. The process of claim 1, wherein the crystallizing (3) comprises a cooling crystallization.

6. The process of claim 4, wherein the evaporation crystallization is carried out in a temperature range of from 50-130° C.

7. The process of claim 4, wherein the evaporation crystallization is carried out over a period of from 1 to 24 hours.

8. The process of claim 4, wherein the evaporation crystallization is carried out discontinuously.

9. The process of claim 4, wherein the evaporation crystallization is carried out continuously.

10. The process of claim 1, wherein the crystallizing (3) is carried out in a crystallizer with an agitator.

11. The process of claim 1, wherein the L-MGDA trialkali metal salt is a L-MGDA trisodium salt.

12. The process of claim 4, wherein the evaporation crystallization is carried out in a temperature range of from 50-120° C.

13. The process of claim 4, wherein the evaporation crystallization is carried out over a period of from 5 to 24 hours.

14. The process of claim 4, wherein the evaporation crystallization is carried out in a temperature range of from 50-100° C.

15. The process of claim 4, wherein the evaporation crystallization is carried out over a period of from 5 to 10 hours.

16. The process of claim 4, wherein the saponifying (2) is carried out in the presence of sodium hydroxide.

17. The process of claim 4, wherein the evaporation crystallization is carried out in a temperature range of from 70-120° C.

18. The process of claim 4, wherein the evaporation crystallization is carried out in a temperature range of from 80-100° C.

* * * * *